United States Patent
Suzuki

(10) Patent No.: US 7,867,191 B2
(45) Date of Patent: Jan. 11, 2011

(54) IRRIGATION/ASPIRATION APPARATUS

(75) Inventor: Nobuo Suzuki, Nukata-gun (JP)

(73) Assignee: Nidek Co., Ltd., Gamagori-Shi (JP)

( * ) Notice: Subject to any disclaimer, the term of this patent is extended or adjusted under 35 U.S.C. 154(b) by 482 days.

(21) Appl. No.: 11/882,391

(22) Filed: Aug. 1, 2007

(65) Prior Publication Data
US 2008/0033349 A1    Feb. 7, 2008

(30) Foreign Application Priority Data
Aug. 1, 2006    (JP) .............................. 2006-210320

(51) Int. Cl.
*A61M 1/00*    (2006.01)
*A61M 37/00*    (2006.01)

(52) U.S. Cl. .............................. 604/35; 604/27; 604/30; 604/31; 604/131; 604/149; 604/151

(58) Field of Classification Search ................. 604/118, 604/119, 27, 30, 35, 131, 140, 149, 151, 604/31; 417/477.2
See application file for complete search history.

(56) References Cited

U.S. PATENT DOCUMENTS 4,246,932 A * 1/1981 Raines ........................ 137/512
4,493,695 A * 1/1985 Cook ........................... 604/27
5,897,524 A * 4/1999 Wortrich et al. ............... 604/30
6,723,065 B2   4/2004 Kishimoto
6,780,166 B2   8/2004 Kanda et al.

FOREIGN PATENT DOCUMENTS

| JP | A-10-043229 | 2/1998 |
| JP | A-2001-170102 | 6/2001 |
| JP | A-2001-212169 | 8/2001 |

* cited by examiner

*Primary Examiner*—Kevin C Sirmons
*Assistant Examiner*—Shefali D Patel
(74) *Attorney, Agent, or Firm*—Oliff & Berridge, PLC

(57) ABSTRACT

To provide an irrigation/aspiration apparatus by which a trouble for an operator is reduced and handling is facilitated and which is capable of preventing a sharp decrease of pressure of an anterior chamber with a simple constitution.

The apparatus has a chamber storing an irrigation liquid, a vent tube for making the liquid flow into an aspiration tube, a leading vent leading the liquid into the chamber from an irrigation tube, an outflow pipe extended in an up-and-down direction, an opening formed on a wall of the outflow pipe, of which a width is narrow and set such that an opening is closed by the liquid under surface tension when a liquid level of the liquid inside the chamber rises, an outflow vent to which the irrigation tube or a vent tube is connected, and an air chamber which is a space provided above an inflow hole of the outflow pipe.

3 Claims, 3 Drawing Sheets

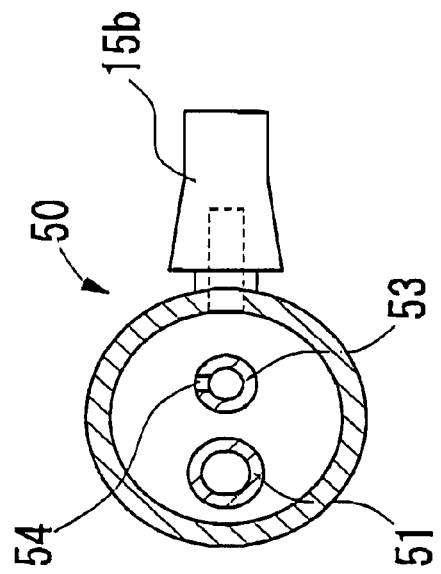
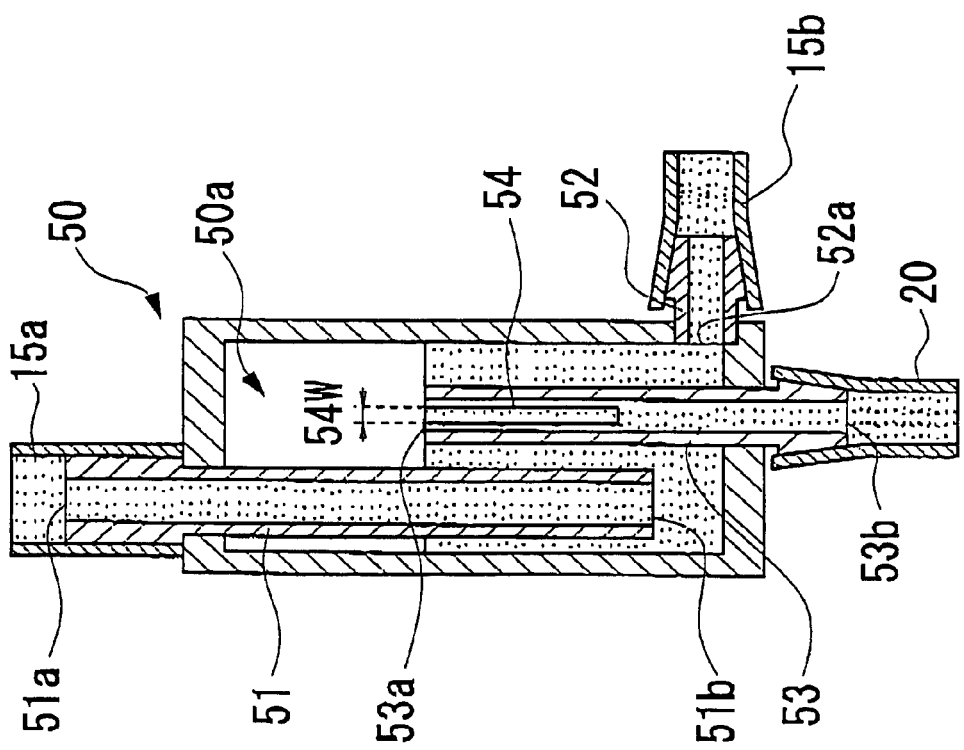
FIG. 3B
FIG. 3A

IRRIGATION/ASPIRATION APPARATUS

BACKGROUND OF THE INVENTION

1. Field of the Invention

The present invention relates to an irrigation/aspiration apparatus used in cataract operation for extracting an opaque crystalline lens.

2. Description of Related Art

There is known an irrigation/aspiration apparatus which supplies an irrigation liquid into an eyeball and aspirates the supplied irrigation liquid with eliminated tissue to be discharged out of the eyeball (e.g., see Japanese Patent Application Unexamined Publication No. Hei 10-43229). The irrigation/aspiration apparatus is used in cataract operation for extracting an opaque crystalline lens. In cataract operation, phacoemulsification which uses a handpiece for fragmentation by means of ultrasonic vibrations (hereinafter, referred to as a US (Ultra Sound) handpiece) is in common use on the ground that phacoemulsification needs only a small incision, and for other reasons.

In phacoemulsification, nucleus of the crystalline lens is fragmented and emulsified by means of ultrasonic vibrations of a US chip attached to the tip of the US handpiece. At the time of fragmentation and emulsification, an irrigation liquid is supplied into the eyeball from the vicinity of the tip of the US chip connected to an irrigation tube. Aspiration pressure is applied to an aspiration tube, one end of which is connected to the Us handpiece by an aspiration pump and the like. The fragmented nucleus of the crystalline lens and the irrigation liquid are aspirated through an aspiration hole of the US handpiece (the US chip) and discharged out of the other end of the aspiration tube.

In phacoemulsification, at the time of aspirating the nucleus of the crystalline lens fragmented by the US chip, if the application of the aspiration pressure by the aspiration pump is continued in a state that the nucleus of the crystalline lens and the like block the aspiration hole of the US chip, the aspiration pressure inside the aspiration pump increases. When the blocking objects such as the nucleus of the crystalline lens on the handpiece are suddenly removed (aspirated) in this state, sharp decrease of pressure of an anterior chamber (surge) temporarily occurs immediately thereafter. When the pressure of the anterior chamber enormously decreases, the anterior chamber is easily deformed. If the anterior chamber is deformed, a corneal endothelium makes contact with the tip of the US chip and the like, and thereby there is a possibility that the corneal endothelium is damaged.

As a measure against the above problem, the above-cited document proposes providing a chamber for storing the irrigation liquid having an air chamber and capable of storing the irrigation liquid, on a channel of the irrigation tube for supplying the irrigation liquid. A technique of the cited document can prevent the sharp decrease of the pressure of the anterior chamber; however, further improvements such as reducing a trouble for an operator, facilitating handling, simplifying a constitution, achieving cost effectiveness and the like are desired.

SUMMARY OF THE INVENTION

An object of the invention is to overcome the problems described above and to provide an irrigation/aspiration apparatus by which a trouble for an operator is reduced and handling is facilitated and which is capable of preventing a sharp decrease of pressure of an anterior chamber with a simple constitution.

To achieve the objects and in accordance with the purpose of the present invention, an irrigation/aspiration apparatus which supplies an irrigation liquid from an irrigation bottle to a patient's eye via an irrigation tube and a handpiece, and aspirates the supplied irrigation liquid with eliminated tissue inside the eye via an aspiration tube connected to the handpiece has a chamber, which is arranged on a channel of the irrigation tube from the irrigation bottle to the handpiece, for storing the irrigation liquid, a vent tube for making the irrigation liquid flow into the aspiration tube by releasing a control valve for reducing residual aspiration pressure of the handpiece, a leading vent for leading the irrigation liquid into the chamber from the irrigation tube on the irrigation bottle side, an outflow pipe extended in an up-and-down direction, of which an inflow hole through which the air and the irrigation liquid inside the chamber flow into the outflow pipe is positioned higher than the leading vent, and to which one of the irrigation tube on the handpiece side and the vent tube is connected, an opening formed on a wall of the outflow pipe, of which a width is narrow and set such that the opening is closed by the irrigation liquid under surface tension when a liquid level of the irrigation liquid inside the chamber rises, and which acts as a path of the irrigation liquid after the irrigation liquid flows into the chamber from the inflow hole, an outflow vent to which the other one of the irrigation tube on the handpiece side and the vent tube is connected, arranged at a position lower than the inflow hole of the outflow tube, and an air chamber which is a space provided above the inflow hole of the outflow pipe, and into which the irrigation liquid is led from the irrigation bottle to compress the air inside the air chamber when an aspiration hole of the handpiece is blocked.

In another aspect of the present invention, an irrigation/aspiration apparatus which supplies an irrigation liquid from an irrigation bottle to a patient's eye via an irrigation tube and a handpiece, and aspirates the supplied irrigation liquid with eliminated tissue inside the eye via an aspiration tube connected to the handpiece has a chamber, which is arranged on a channel of the irrigation tube from the irrigation bottle to the handpiece, for storing the irrigation liquid, including a leading vent for leading the irrigation liquid into the chamber from the irrigation tube on the irrigation bottle side, an outflow pipe extended in an up-and-down direction, of which an inflow hole through which the air and the irrigation liquid inside the chamber flow into the outflow pipe is positioned higher than the leading vent, and which is connected to the aspiration tube on the handpiece side, an air chamber provided above the inflow hole, in which the air is compressed by leading the irrigation liquid from the irrigation bottle when an aspiration hole of the handpiece is blocked, and an opening formed on a wall of the outflow pipe, which is narrow in width and set such that the opening is closed by the irrigation liquid under surface tension when a liquid level of the irrigation liquid inside the chamber rises, and which acts as a path of the irrigation liquid after the irrigation liquid flows into the chamber from the inflow hole by the rise of the liquid level of the irrigation liquid.

Yet, in another aspect of the present invention, an irrigation/aspiration apparatus which supplies an irrigation liquid to a patient's eye, and aspirates the supplied irrigation liquid via an aspiration tube has an irrigation tube and a handpiece for supplying the irrigation liquid to the patient's eye, a chamber arranged on a channel of the irrigation tube and having a leading vent from which the irrigation liquid is led, an outflow pipe of which an inflow hole through which the irrigation liquid inside the chamber flows into is positioned higher than the leading vent, and an opening which is formed on a wall of the outflow pipe, and has a width such that the opening is blocked by the irrigation liquid under surface tension when a liquid level of the irrigation liquid inside the chamber rises, and that the irrigation liquid is capable of flowing through the opening after the irrigation liquid flows into the outflow pipe through the inflow hole.

Additional objects and advantages of the invention are set forth in the description which follows, are obvious from the description, or may be learned by practicing the invention. The objects and advantages of the invention may be realized and attained by the apparatus in the claims.

BRIEF DESCRIPTION OF THE DRAWINGS

The accompanying drawings, which are incorporated in and constitute apart of this specification, illustrate embodiments of the present invention and, together with the description, serve to explain the objects, advantages and principles of the invention. In the drawings.

FIGS. 3A and 3B are views for illustrating a configuration of a chamber for storing an irrigation liquid;

DETAILED DESCRIPTION OF THE PREFERRED EMBODIMENTS

Figure 1:
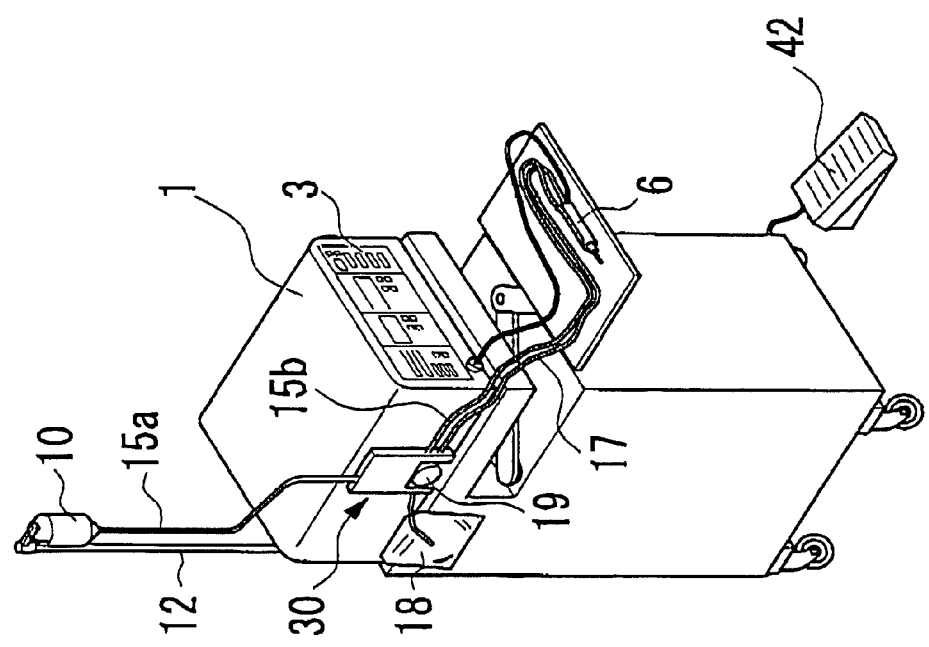
FIG. 1 is a schematic external view of an irrigation/aspiration apparatus according to the preferred embodiment of the present invention.
Figure 2:
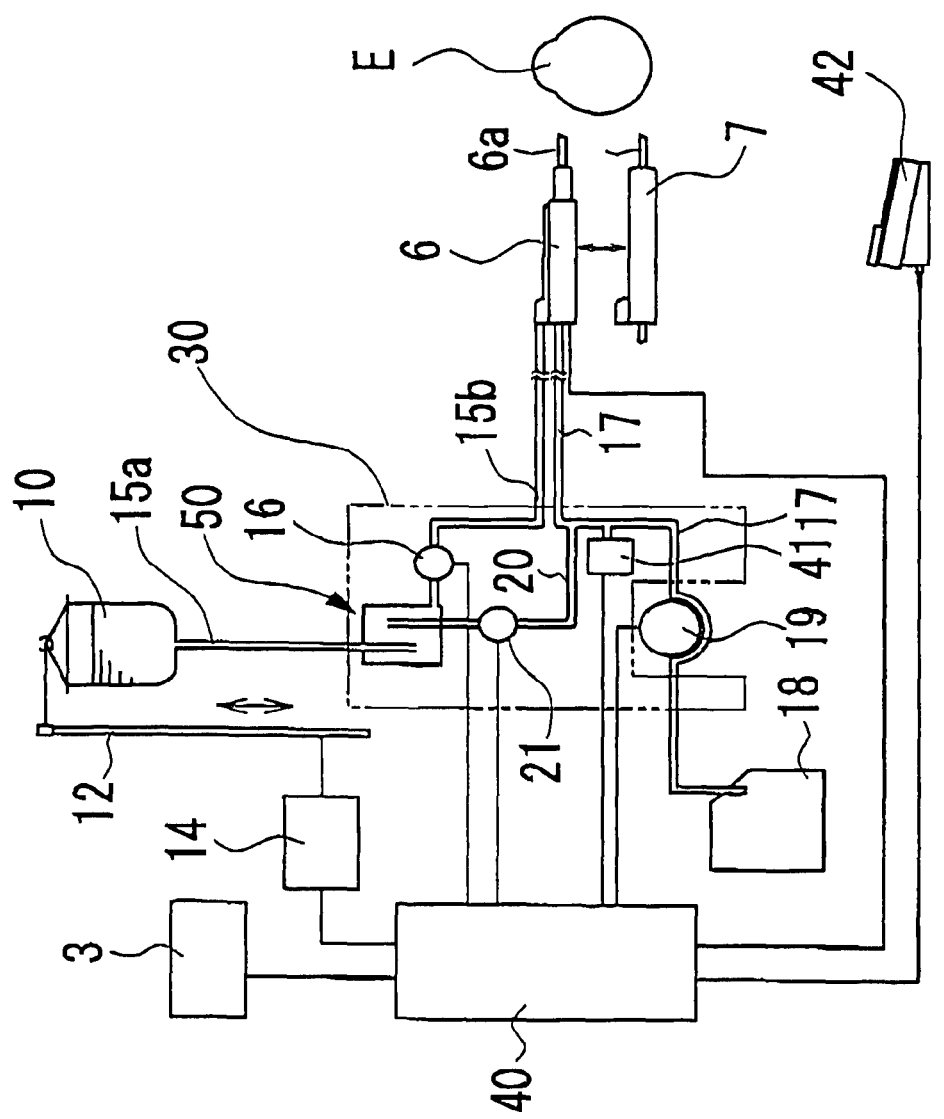
FIG. 2 is a view showing a schematic configuration of relevant elements of the apparatus.

A detailed description of one preferred embodiment of an irrigation/aspiration apparatus embodied by the present invention is provided below with reference to the accompanying drawings. FIG. 1 is a schematic external view of an ophthalmic irrigation/aspiration apparatus used in cataract operation. FIG. 2 is a view showing a schematic configuration of relevant elements of the apparatus.

A main body 1 of the apparatus houses a control part 40. An operation panel (input part) 3 for inputting a signal for setting operation conditions and the like is placed on the front of the main body 1. An irrigation bottle 10 containing an irrigation liquid such as a saline which is supplied to a patient's eye E, is hung on a pole 12. The pole 12 is moved up and down by an up-and-down driving apparatus 14 and is capable of changing a height of the irrigation bottle 10. Irrigation pressure is adjusted so as to supply the patient's eye E with the irrigation liquid at proper fluid pressure (quantity of flow or irrigation speed) according to the height at which the irrigation bottle 10 is set. An irrigation tube 15a and an irrigation tube 15b guide the irrigation liquid which drops from the irrigation bottle 10 to the patient's eye E. One end of the irrigation tube 15a and one end of the irrigation tube 15b are connected to a chamber 50, which is provided in a cassette 30, for storing the irrigation liquid. The cassette 30 is a disposable cassette made of resin and the like, in which channels for irrigation/aspiration are formed. The cassette 30 is freely attached to and detached from the main body 1.

A control valve 16 such as a pinch valve is provided midway along the irrigation tube 15b connected to the chamber 50. Flow of the irrigation liquid is controlled by opening or closing the control valve 16. The other end of the irrigation tube 15b is connected to various kinds of handpieces such as a US handpiece 6 for fragmentation and an I/A handpiece 7 for irrigation/aspiration. A US chip 6a attached to the tip of the US handpiece 6 fragments and emulsifies nucleus of a crystalline lens by using ultrasonic vibrations. The US chip 6a includes an aspiration hole and aspirates the fragmented nucleus of the crystalline lens and the irrigation liquid via the aspiration hole. Appropriate handpieces are selected among the various kinds of the handpieces such as the US handpiece 6 and the I/A handpiece 7 according to a step in operation, a method of operation and the like, and the selected ones are replaced with previously used ones to be used.

The US handpiece 6 is connected to an aspiration tube 17 which discharges the irrigation liquid and the fragmented nucleus of the crystalline lens aspirated from the tip of the US chip 6a. In a rear portion of the aspiration tube 17, a part thereof is placed inside the cassette 30. A rear end of the aspiration tube 17 is located in a waste liquid bag 18. An aspiration pump 19 for generating aspiration pressure is provided midway along the aspiration tube 17 in the cassette 30. The control part 40 drives and controls the aspiration pump 19 to adjust quantity of aspiration flow thereof. The aspirated waste liquid is discharged into the waste liquid bag 18.

A pressure sensor 41 is provided midway along the aspiration tube 17 at a nearer position to the handpiece 6 side than a position of the aspiration pump 19 and in the cassette 30. In addition, one end of a vent tube 20 is connected to a midpoint of the aspiration tube 17 in the cassette 30. The other end of the vent tube 20 is connected to the chamber 50. A control valve 21 such as a pinch valve is provided midway along the vent tube 20. Quantity of the irrigation liquid flowing from the vent tube 20 into the aspiration tube 17 is controlled by opening or closing the control valve 21. The vent tube 20 is used to reduce residual aspiration pressure of the aspiration tube 17 when the aspiration by the aspiration pump 19 is stopped. The pressure sensor 41 detects the aspiration pressure inside the aspiration tube 17 at all times. When the aspiration pressure increases above a set value, the control part 40 controls to stop driving of the aspiration pump 19. An upper limit of the aspiration pressure (the maximum aspiration pressure) is set by operating switches on the operation panel 3.

The irrigation liquid and the fragmented nucleus of the crystalline lens in the patient's eye E are aspirated from the aspiration hole of the US chip 6a to be discharged into the waste liquid bag 18 via the aspiration tube 17. The control part 40 controls the quantity of aspiration flow and the aspiration pressure by driving and controlling the aspiration pump 19 based on a positional signal corresponding to a pushing position of a footswitch 42 or set values set by the operation panel 3.

Next, a detailed description will be given to a configuration of the chamber 50. FIG. 3A is a vertical sectional view sectioned on the center in a horizontal direction of the chamber 50. FIG. 3B is a sectional view horizontally sectioned on the center in an up-and-down direction of the chamber 50. In FIG. 3A, a leading pipe 51 for the irrigation liquid extends from a position above the chamber 50 into the chamber 50 toward a bottom face of the chamber 50. A vent 51a at an upper end of the leading pipe 51 is connected to the irrigation tube 15a extending from the irrigation bottle 10. A leading vent 51b at a lower end of the leading pipe 51 is located in the vicinity of the bottom face of the chamber 50. An outflow pipe 52 having a vent 52a for the irrigation liquid is formed at a right-side lower portion of the chamber 50 in FIG. 3A. The outflow pipe 52 is connected to the irrigation tube 15b extending to the handpiece 6 side. It is preferable that the outflow pipe 52 is formed at the lowest portion of the chamber 50 so that the irrigation liquid stored in the chamber 50 flows out efficiently.

In addition, the chamber 50 includes an outflow pipe 53 extending in the up-and-down direction. An outflow hole 53b at a lower end of the outflow pipe 53 is connected to the vent tube 20. An inflow hole 53a at an upper end of the outflow pipe 53 is set at a position which is higher than the leading vent 51b at the lower end of the leading pipe 51 and provides a space in an upper portion inside the chamber 50. In this preferred embodiment, a position of the inflow hole 53a is set so that a capacity of about 10 cc is provided inside the chamber 50 and a capacity of about 5 cc is provided in a space 50a above the inflow hole 53a.

An opening 54 being narrow in width and extending in the up-and-down direction is formed on a wall of the outflow pipe 53 which is formed in the up-and-down direction inside the chamber 50. In the preferred embodiment in FIG. 3A, the opening 54 is formed as a notch continuously extending up to the inflow hole 53a. The lowest end of the opening 54 is set at a position a little higher than that of the leading vent 51b at the lower end of the leading pipe 51. A width 54W of the opening 54 is set such that, when the irrigation liquid is led into the chamber 50 through the leading pipe 51 and a liquid level of the irrigation liquid inside the chamber 50 rises (details will be described later), the opening 54 is closed by a water film formed by surface tension of the irrigation liquid (i.e., the irrigation liquid does not flow into the outflow pipe 53 under surface tension of the irrigation liquid). In this preferred embodiment, the width 54W of the opening 54 is about 1 mm, which is smaller than inner diameters of the vent tube 20 and the irrigation tube 15b. An inner diameter of the outflow pipe 53 is about 2 mm.

In addition, in FIG. 3A, the outflow pipe 53 is formed vertically in the up-and-down direction in order to facilitate manufacturing; however, the present invention includes a configuration in which the outflow pipe 53 extends obliquely in the up-and-down direction. It is essential only that the opening 54 is placed below the inflow hole 53a of the outflow pipe 53. In addition, the outflow pipe 53 may be formed to be integral with a wall of the chamber 50.

An operation of the irrigation/aspiration apparatus having the above-mentioned configuration will be described. In the preferred embodiment, described is cataract operation in which phacoemulsification is performed on the opaque crystalline lens with the US handpiece 6 to aspirate and remove the emulsified crystalline lens.

Before operation, the irrigation bottle 10 and the cassette 30 are attached to the main body 1, the tubes are attached to the leading pipe 51 and outflow pipes 52 and 53 of the chamber 50 and the US handpiece 6, and other necessary preparations are made. The irrigation bottle 10 is positioned at an appropriate height in synchronization with the pole 12 by the up-and-down driving apparatus 14 based on the quantity of the irrigation fluid set by the switches on the operation panel 3.

In addition, as a preparation, an operator infuses the irrigation liquid into the chamber 50 and the tubes. First, the operator operates the switches on the operation panel 3 to open the control valve 21 in a state where the control valve 16 is closed, and then to drive the aspiration pump 19. By driving the aspiration pump 19, the aspiration pressure is generated in a channel from the vent tube 20 to the aspiration pump 19. The air inside the chamber 50 is aspirated under the aspiration pressure through the inflow hole 53a and the opening 54 of the outflow pipe 53. And the air is to be discharged out of the tip of the aspiration tube 17 extending up to the waste liquid bag 18. Thereby, the irrigation liquid in the irrigation bottle 10 is gradually stored in the chamber 50. When the aspiration of the air inside the chamber 50 by the aspiration pump 19 continues, a liquid level of the irrigation liquid inside the chamber 50 gradually rises to go above the leading vent 51b at the lower end of the leading pipe 51. And the water level rises to go above the opening 54 of the outflow pipe 53. At this time, the opening 54 is closed by the water film formed by surface tension, and thereby the liquid level of the irrigation liquid inside the chamber 50 continues to rise and finally reaches the inflow hole 53a at the upper end of the outflow pipe 53.

When the liquid level of the irrigation liquid goes above the inflow hole 53a, the aspiration of the air inside the chamber 50 is ended and the irrigation liquid starts to flow into the inflow hole 53a. When the irrigation liquid flows into the outflow pipe 53, the water film which separates an interior of the outflow pipe 53 from an exterior of the outflow pipe 53 by the surface tension at the position of the opening 54 is broken. And the irrigation liquid starts to flow into the outflow pipe 53 also through the opening 54 (the opening 54 also act as a path of the irrigation liquid). Then, the irrigation liquid is filled in from the vent tube 20 via the aspiration tube 17 up to the aspiration pump 19. When the irrigation liquid starts to flow out of the tip of the aspiration tube 17, the infusion of the irrigation liquid into the chamber 50 is completed. At this time, the liquid level of the irrigation liquid inside the chamber 50 rises up to approximately the same level as the position of the inflow hole 53a. And the space 50a formed at the upper portion inside the chamber 50 acts as an air chamber. The air inside the air chamber is compressed corresponding to the height of the irrigation bottle 10.

Next, the operator operates the switches on the operation panel 3 to open the control valve 16 in a state where the control valve 21 is closed, and to infuse the irrigation liquid into the irrigation tube 15b connected to the outflow pipe 52, the handpiece 6 and the aspiration tube 17. The US tip 6a of the handpiece 6 is covered with a known airtight cap called a test chamber. Then, the irrigation liquid is made to flow into the aspiration tube 17 from the aspiration hole of the US chip 6a. When the aspiration pump 19 is driven, the air inside the aspiration tube 17, the air inside the channel of the handpiece 6 and the air inside the irrigation tube 15b are aspirated to be discharged out of the end of the aspiration tube 17 on the waste liquid bag 18 side. Thereby, the irrigation liquid inside the chamber 50 flows out from the outflow pipe 52 and the irrigation liquid flows into all irrigation channels from the irrigation tube 15b to the aspiration tube 17.

When the driving of the aspiration pump 19 is stopped and the control valve 16 is closed, the discharge of the irrigation liquid is stopped. Since the irrigation liquid is resupplied into the chamber 50 from the irrigation bottle 10, the liquid level of the irrigation liquid inside the chamber 50 is kept at approximately the same level as the position of the inflow hole 53a. And the air in the air chamber (the space 50a) is kept to be compressed at pressure corresponding to the height of the irrigation bottle 10.

An operation in surgery will be described. The operator, while observing the patient's eye E using an unillustrated surgical microscope, incises a sclera and an anterior lens capsule. And then, he/she inserts the US chip 6a into the eyeball through an incision. The US chip 6a is inserted into the eyeball by pushing the footswitch 42 up to a position for performing only irrigation operation to close the control valve 21 and open the control valve 16, while making the irrigation liquid flowing out from the handpiece 6. When the irrigation liquid is supplied into the eyeball, the pressure of the anterior chamber is maintained at the pressure corresponding to the height of the irrigation bottle 10.

After sufficiently obtaining depth of the anterior chamber by supplying the irrigation liquid into the eyeball, the operator pushes the footswitch 42 up to a position for performing aspiration in addition to the irrigation in order to perform the aspiration. The control part 40 drives the aspiration pump 19 according to the signal from the footswitch 42 in order to aspirate the irrigation liquid at a set quantity of aspiration flow. In a state where the aspiration hole is released, the irrigation liquid inside the anterior chamber is aspirated from the aspiration hole of the US chip 6a via the aspiration tube 17 under the aspiration pressure generated by aspirating the irrigation liquid by the set quantity of aspiration flow (hereinafter, referred to as reference aspiration pressure).

In addition, when the operator, in order to fragment and emulsify the nucleus of the crystalline lens, pushes the footswitch 42 up to a position for performing ultrasonic vibration operation in addition to the irrigation operation and the aspiration operation, the control part 40 controls the US chip 6a to generate ultrasonic vibrations.

If the nucleus of the crystalline lens blocks the aspiration hole at the tip of the US chip 6a during the aspiration, the aspiration pressure inside the aspiration tube 17 increases above the reference aspiration pressure. When the aspiration pressure, which is detected by the pressure sensor 41, reaches the set value, the aspiration pump 19 is stopped to fix the aspiration pressure of the handpiece 6 at the set value. When the blockage of the US chip 6a is eliminated in this state, the irrigation liquid larger than the set quantity of aspiration flow is temporarily aspirated from the anterior chamber.

In the case of not providing the chamber 50, the supply of the irrigation liquid cannot catch up with the temporary increase of the quantity of aspiration flow due to rising of the aspiration. Accordingly, the pressure of the anterior chamber temporarily decreases (a surge). In contrast, in the apparatus of the present invention, the chamber 50 is provided between the irrigation tube 15a and the irrigation tube 15b for supplying the irrigation liquid. When the aspiration hole of the US chip 6a is blocked, the irrigation liquid having the same pressure as the irrigation pressure corresponding to the height of the irrigation bottle 10 is stored in the chamber 50 in a state where the air inside the space 50a (air chamber) is compressed. When the blocking objects are eliminated from the aspiration hole of the US chip 6a and the pressure of the anterior chamber decreases, the compressed air inside the space 50a (air chamber) expands in synchronization with the decrease and a force to push down the irrigation liquid inside the chamber 50 is exerted. The irrigation pressure to push down the irrigation liquid has the same level as the irrigation pressure corresponding to the height of the irrigation bottle 10. However, compared with leading the irrigation liquid to the handpiece 6 directly from the irrigation bottle 10, leading the irrigation liquid from the chamber 50 to the handpiece 6 needs a shorter length of the channel of the irrigation tube, and thereby pipe resistance due to viscosity of the irrigation liquid or the like can be reduced and the irrigation liquid is smoothly supplied to the eyeball. Accordingly, even if a sudden aspiration is performed, the irrigation liquid can be quickly supplied and the temporary decrease of the pressure of the anterior chamber (the surge) can be moderated.

When the pressure of the anterior chamber of the eyeball is brought into an original steady state and the inflow of the irrigation liquid from the irrigation bottle 10 catches up with the quantity of aspiration flow, the liquid level of the irrigation liquid inside the chamber 50 recovers an initial state and the air inside the space 50a (the air chamber) is brought into the compressed state again.

In addition, when a signal for releasing the aspiration pressure of the handpiece 6 is inputted by pushing the footswitch 42, the control part 40 controls to open the control valve 21 for the vent tube 20 side. As a result, the irrigation liquid inside the irrigation bottle 10 and the chamber 50 starts to flow into the aspiration tube 17 via the vent tube 20. Thereby, the aspiration pressure of the handpiece 6 is reduced. At this time, since the irrigation liquid inside the chamber 50 flows into the opening 54 formed on the wall of the outflow pipe 53, the irrigation liquid is sufficiently supplied to the vent tube 20 side even if the liquid level of the irrigation liquid goes below the inflow hole 53a. In addition, as in the case of eliminating the blockage on the handpiece 6, the compressed air inside the space 50a (the air chamber) expands in synchronization with the release of the control valve 21, which facilitates the supply of the irrigation liquid inside the chamber 50 to the vent tube 20 side. Thereby, a response of decreasing the aspiration pressure is made quicker than a case where the chamber 50 is not connected with the vent tube 20. When the aspiration pressure recovers the steady state and the supply of the irrigation liquid from the irrigation bottle 10 catches up with the quantity of aspiration flow, the liquid level of the irrigation liquid inside the chamber 50 recovers the original level.

The chamber 50 as described above has a simple configuration that a dedicated driving mechanism or a dedicated movable part for infusing the irrigation liquid into the chamber 50 is not included, which brings about an advantage of cost effectiveness. Such a simple configuration is especially suitable for the configuration in which the chamber 50 is integrally included in the disposable cassette 30 as described in the preferred embodiment. In addition, the chamber 50 of the apparatus of the present invention does not include the dedicated driving system or the dedicated movable part, which facilitates handling. In addition, a trouble for the operator is reduced.

The configuration of the chamber 50 is not limited to the one shown in FIGS. 3A and 3B. The width 54W of the opening 54 formed on the wall of the outflow pipe 53 may be set such that the surface tension of the irrigation liquid is maintained at the time of infusing the irrigation liquid, and the surface tension can be maintained even if the width 54W is a little wider than 1 mm. In addition, the surface tension of the irrigation liquid can be sufficiently maintained when the width 54W of the opening 54 is narrower than 1 mm. However, if the width 54W is too narrow, inflow quantity of the irrigation liquid becomes small, which is disadvantageous. In addition, the opening 54 does not need to be formed continuously to the inflow hole 53a at the upper end of the outflow pipe 53. And the opening 54 may be formed partway or may be formed in a plurality of holes. In addition, the lower end of the opening 54 may be placed closer to the bottom face of the chamber 50. However, if the lower end of the opening 54 is placed below the leading vent 51b at the lower end of the leading pipe 51, bubbles of the air mixed in the irrigation liquid flowing from the irrigation bottle 10 are apt to flow into the outflow pipe 53 through the opening 54. Thereby, it is preferable that the lowest end of the opening 54 is placed at a position higher than the leading vent 51b at the lower end of the leading pipe 51. If the opening 54 is placed higher than the leading vent 51b, the bubbles mixed in the irrigation liquid flowing from the leading pipe 51 arc stored in the space 50a, and the inflow of the bubbles into the outflow pipe 53 can be prevented.

Figure 4:
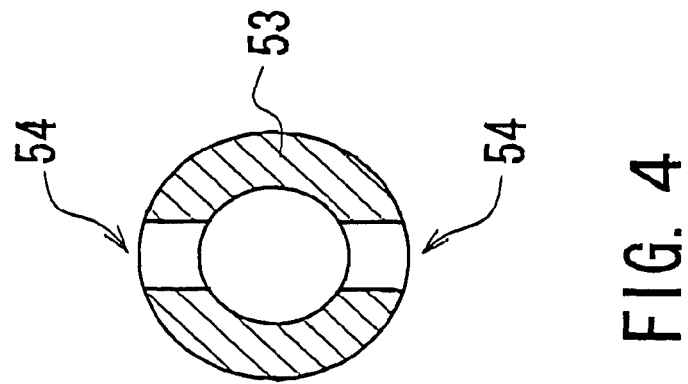
FIG. 4 is a view showing a modified embodiment of an opening of an outflow tube in the chamber.

Further, a plurality of openings 54 may be formed as shown in FIG. 4. In addition, it is preferable that a total area of the opening 54 is larger than an area of an aperture of the inflow hole 53a. If the total area of the opening 54 is too smaller than the area of the aperture of the inflow hole 53a, the air in the space 50a (the air chamber) above the Inflow hole 53a is apt to be drawn into the inflow hole 53a when the control valve 21 is opened to draw the irrigation liquid into the outflow pipe 53. As a result, the air unintentionally flows into the aspiration tube 17. The above-mentioned configuration is preferable for preventing the flow of the air into the aspiration tube 17.

Incidentally, it is preferable that the vent 52a of the outflow pipe 52 is positioned in the vicinity of the bottom face of the chamber 50 in order to efficiently supply the irrigation liquid inside the chamber 50 to the irrigation tube 15b side. It is essential only that the vent 52a of the outflow pipe 52 is positioned at least below the inflow hole 53a of the outflow pipe 53, and below the decreased liquid level of the irrigation liquid at the time of the surge.

In addition, a state in FIG. 2 is preferable for connections of the irrigation tube 15b and the vent tube 20 to the outflow pipe 52 and the outflow pipe 53, respectively. However, the reverse connections may be employed. That is to say, the outflow pipe 52 may be connected to the vent tube 20, and the outflow pipe 53 may be connected to the irrigation tube 15b.

Figure 5:
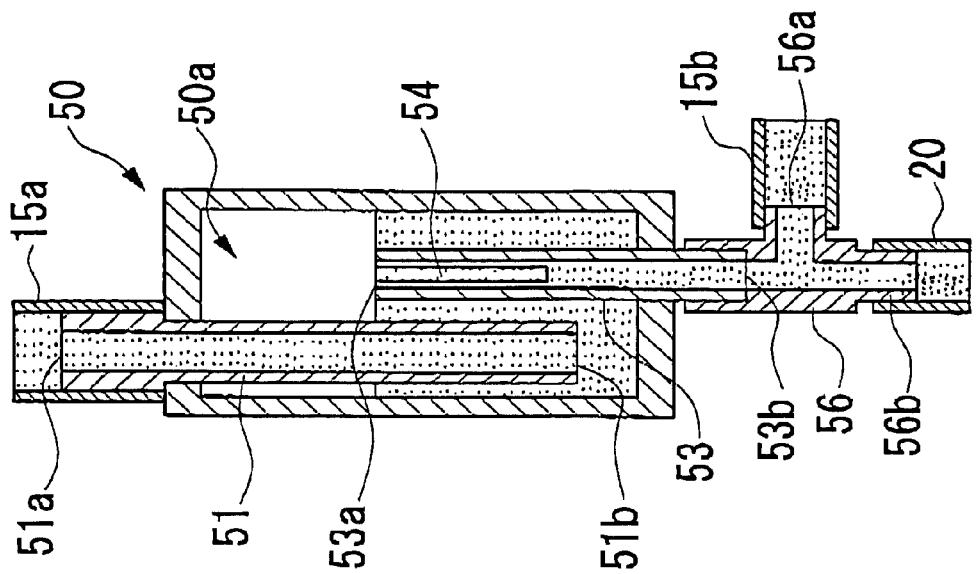
FIG. 5 is a view showing a configuration of a modified embodiment of the chamber.

FIG. 5 is a view showing a configuration of a modified embodiment of the chamber 50. In the chamber 50 shown in FIG. 5, a channel dividing member 56 is connected to the outflow hole 53b. A bifurcating channel 56a is connected to the irrigation tube 15b, and a bifurcating channel 56b is connected to the vent tube 20. This embodiment as shown in FIG. 5 includes the same elements as the preferred embodiment as shown in FIG. 3 except for the outflow pipe 52. In this embodiment, the outflow pipe 53 doubles as an outflow pipe connected to the irrigation tube 15b and the vent tube 20. The opening 54 formed on the wall of the outflow pipe 53 acts as an inflow vent for the irrigation liquid.

In this embodiment, if the handpiece 6 connected to the irrigation tube 15b is placed below the chamber 50, the irrigation liquid is infused into the chamber 50 by a natural drop of the irrigation liquid according to the height of the irrigation bottle 10. Then, the liquid level of the irrigation liquid automatically rises up to the inflow hole 53a in the state where the opening 54 is closed by surface tension of the irrigation liquid. Thereby, the trouble for the operator is further reduced.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An irrigation/aspiration apparatus which supplies an irrigation liquid from an irrigation bottle positioned at a given height to a patient's eye via an irrigation tube and a handpiece connected to the irrigation tube, and aspirates the supplied irrigation liquid with eliminated tissue inside the eye via the handpiece and an aspiration tube connected to the handpiece, the apparatus comprising:

a pump for generating aspiration pressure inside the aspiration tube;
a chamber, which is arranged on a channel of the irrigation tube from the irrigation bottle to the handpiece, for storing air and the irrigation liquid;
a first control valve, which is arranged on a channel of the irrigation tube from the chamber to the handpiece;
a vent tube for connecting the chamber with the aspiration tube on the handpiece side with respect to the pump;
a second control valve, which is arranged on a channel of the vent tube;
a leading vent, which is positioned at a lower portion inside the chamber, for leading the irrigation liquid into the chamber from the irrigation tube on the irrigation bottle side;
an outflow hole, which is positioned at the lower portion inside the chamber or on the channel of the vent tube, for flowing the irrigation liquid into the irrigation tube on the handpiece side from the chamber;
an outflow pipe extended in an up-and-down direction inside the chamber, of which an inflow hole through which the air and the irrigation liquid inside the chamber flow into the outflow pipe is positioned higher than the leading vent and is disposed to leave a given space at an upper portion inside the chamber, and to which the vent tube is connected;
an opening that is formed on a wall of the outflow pipe, is arranged at a position higher than the leading vent and lower than the inflow hole, has a narrow width that is set such that the opening is closed by surface tension of the irrigation liquid during a time from when a liquid level of the irrigation liquid inside the chamber rises by leading the irrigation liquid from the leading vent to when the liquid level of the irrigation liquid reaches the inflow hole, and acts as a path of the irrigation liquid after the irrigation liquid flows into the outflow pipe from the inflow hole by a further rise of the liquid level of the irrigation liquid; and
a control part that controls driving of each of the pump, the first control valve, and the second control valve such that the irrigation tube, the aspiration tube, and the vent tube are filled with the irrigation liquid and the chamber is filled with the irrigation liquid leaving a given space,
wherein the air inside the given space inside the chamber filled with the irrigation liquid is compressed corresponding to a height of the irrigation bottle.

2. The irrigation/aspiration apparatus according to claim 1, wherein
the opening is formed continuously in an up-and-down direction or formed in a plurality of holes on the wall of the outflow pipe, and a total area of the opening is larger than an area of the inflow hole.

3. An irrigation/aspiration apparatus which supplies an irrigation liquid from an irrigation bottle positioned at a given height to a patient's eye via an irrigation tube and a handpiece connected to the irrigation tube, and aspirates the supplied irrigation liquid with eliminated tissue inside the eye via the handpiece and an aspiration tube connected to the handpiece, the apparatus comprising:

a pump for generating aspiration pressure inside the aspiration tube;
a chamber having a leading pipe and an outflow pipe inside, in which the irrigation liquid from the irrigation bottle flows into the chamber via the irrigation tube and the leading pipe, an opening is formed on a wall of the outflow pipe, the opening has a narrow width such that the irrigation liquid does not flow into the outflow pipe from the opening by surface tension of the irrigation liquid unless the irrigation liquid flows into the outflow pipe from an inflow hole provided at an upper portion of the outflow pipe, a closed space is formed above the outflow pipe by a rise of a liquid level of the irrigation liquid inside the chamber so as to compress air in the closed space, and the irrigation liquid is supplied to the handpiece via the irrigation tube from an outflow hole provided at a lower portion of the chamber or the outflow pipe;

a vent tube in which one end of a channel is connected to an aspiration channel and the other end of the channel is connected to an irrigation channel;

a first control valve provided to the irrigation channel from the chamber;

a second control valve provided to the channel of the vent tube; and a control part that controls driving of each of the pump, the first control valve, and the second control valve.

\* \* \* \* \*